US012050725B2

United States Patent
Gompertz

(10) Patent No.: US 12,050,725 B2
(45) Date of Patent: *Jul. 30, 2024

(54) METHOD FOR DETECTING VOLUNTARY MOVEMENTS OF STRUCTURES IN THE EAR TO TRIGGER USER INTERFACES

(71) Applicant: Earswitch Ltd, Hertfordshire (GB)

(72) Inventor: Nicholas Gompertz, Bruton (GB)

(73) Assignee: Earswitch Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/115,191

(22) Filed: Feb. 28, 2023

(65) Prior Publication Data
US 2023/0205310 A1    Jun. 29, 2023

Related U.S. Application Data

(63) Continuation of application No. 17/253,201, filed as application No. PCT/GB2019/051357 on May 16, 2019, now Pat. No. 11,669,153.

(30) Foreign Application Priority Data

Jun. 19, 2018 (GB) ...................... 1810082

(51) Int. Cl.
*G06F 3/01* (2006.01)
*G06F 3/0482* (2013.01)
(Continued)

(52) U.S. Cl.
CPC ............ *G06F 3/011* (2013.01); *G06F 3/0482* (2013.01); *H04N 5/33* (2013.01); *H04R 1/1041* (2013.01)

(58) Field of Classification Search
CPC ........ G06F 3/011; G06F 3/0482; G06F 3/017; G06F 3/0304; H04N 5/33; H04R 1/1041;
(Continued)

(56) References Cited

U.S. PATENT DOCUMENTS

| 5,711,308 | A | * | 1/1998 | Singer | .................... G01H 9/008 600/559 |
| 11,669,153 | B2 | * | 6/2023 | Gompertz | ................ H04N 5/33 345/156 |

(Continued)

FOREIGN PATENT DOCUMENTS

WO    WO-2014117956 A2 *  8/2014    ......... A61B 1/00009

OTHER PUBLICATIONS

International Search Report and Written Opinion for International Application No. PCT/GB2019/051357, dated Aug. 21, 2019, 11 pages. 2019.

(Continued)

*Primary Examiner* — Lunyi Lao
*Assistant Examiner* — Jarurat Suteerawongsa
(74) *Attorney, Agent, or Firm* — Buchanan Ingersoll & Rooney PC

(57) ABSTRACT

A sensor which detects voluntary movements of ear structures, including the ear drum complex, which triggers user interfaces of electronic devices to enable communication and other activities by interaction with assistive technology. The method of detecting this voluntary movement may also be used to trigger and control user interfaces in connected devices such as mobile telephones and incorporated into multi-function earphones.

24 Claims, 8 Drawing Sheets

(51) Int. Cl.
*H04N 5/33* (2023.01)
*H04R 1/10* (2006.01)

(58) Field of Classification Search
CPC .. H04R 25/00; H04R 2430/01; H04R 1/1091;
A61F 4/00
See application file for complete search history.

(56) References Cited

U.S. PATENT DOCUMENTS

| | | | |
|---|---|---|---|
| 2011/0200213 A1 | 8/2011 | Knox | |
| 2012/0001846 A1* | 1/2012 | Taniguchi | G06F 1/163 |
| | | | 345/156 |
| 2013/0303941 A1* | 11/2013 | Porges | A61B 5/125 |
| | | | 600/559 |
| 2018/0081621 A1 | 3/2018 | Dusan et al. | |
| 2018/0167716 A1* | 6/2018 | Fujimoto | G01J 1/0204 |

OTHER PUBLICATIONS

Entire patent prosecution history of U.S. Appl. No. 17/253,201, filed Dec. 17, 2020, entitled, "Method for Detecting Voluntary Movements of Structures in the Ear to Trigger User Interfaces."

* cited by examiner

METHOD FOR DETECTING VOLUNTARY MOVEMENTS OF STRUCTURES IN THE EAR TO TRIGGER USER INTERFACES

CROSS-REFERENCE TO RELATED APPLICATIONS

This application is a continuation patent application of U.S. patent application Ser. No. 17/253,201, filed Dec. 17, 2020, which is a U.S. national phase application filed under 35 U.S.C. § 371 claiming benefit to International Patent Application No. PCT/GB2019/051357, filed May 16, 2019, which claims priority to GB Patent Application No. 1810082.6, filed Jun. 19, 2018, the contents of these applications being incorporated by reference in their entirety.

BACKGROUND OF THE INVENTION

Some people with motor disabilities (disabilities that prevent normal control of muscular function), cannot communicate normally, as they are unable to generate speech. People with severe disabilities may be able to use existing assistive technologies using switches that are triggered by movements that they are still able to control, such as cheek movements, eye movements (such as by eye tracking) or head movement.

Simple switch technology has been used to allow people with communication difficulties due to motor problems (difficulty controlling muscle movement), such as cerebral palsy, multiple sclerosis, motor neurone disease or with neck trauma, to interface with communication aids and other user interfaces. These user interfaces can control electronic devices such as electronic wheelchairs, computers and other user interface outputs to assist with communication, mobility, activities of daily living and entertainment (assistive technologies) and other functions.

Communication aids can allow users to select a letter or word on a graphical user interface, by simple switch activation during scanning of an on screen keyboard display, or activate a function by selecting an icon, as well as other output options.

Some people with the most severe disabilities may find it difficult to control the movements that are currently detectable and used to trigger assistive technology. This may be due to absence of control of the muscles that can be used to trigger an existing switch, or due to abnormal involuntary uncontrollable movements which interfere with detection of more subtle voluntary movements. An example of this is if a person has athetoid involuntary movements, causing unpredictable involuntary head movements which interfere with eye tracking technology or the ability of a purposeful head movement to trigger a switch.

Other prior art (US20180081621) ASSISTIVE APPARATUS HAVING ACCELEROMETER-BASED ACCESSIBILITY); uses an in ear device containing accelerometers which detect audible "hums" generated by the user, in conjunction with head tilts, to generate inputs to assistive technology. This relies on the users ability to phonate (create sound), and so is less likely to help those users whose disability is so severe that they cannot use existing assistive technology switches, as they are less likely to be able generate the required "hums". Also, other people who may not be able to generate sufficient "hums" are those who have neck trauma, who may have damaged the recurrent laryngeal nerve which controls the voice box (larynx), and other people who have poor vocal cord control and people with a tracheostomy (breathing tube in the neck). This method also does not provide a silent and invisible means of controlling electronic devices worn in the ear or ear canal, sometimes known as smart "hearable" devices Tympanic membrane (ear drum) and attached middle ear structures, such as the adjacent ossicular bone (the malleus bone), can be moved by muscles within the middle ear such as the tensor tympani muscle that is attached to the malleus. This combination of the ear drum and malleus will subsequently be referred to as the ear drum complex. Contraction of this tensor tympani is reported to help muffle the hearing during chewing, and to protect the hearing in response to loud noises. It has been noted that some people have voluntary control of this muscle and contraction can be heard by the individual as a rumbling noise. The muscle can also be triggered during strong eyelid closing and yawning.

Voluntary movement of the ear drum complex is visible, and has been recorded using a video auroscope (camera placed within the ear canal with LED light source), which is small enough to fit within an ear canal located sensor. Movement of the handle of the malleus has been measured and tracked using software imaging analysis. Voluntary movement of the ear canal is also visible and detectable, which may be due to the connection of the origin of the tensor tympani muscle to the cartilaginous eustachian tube, which is a continuation of the ear cavity internally, or through the contemporaneous contraction of associated muscles.

Other recorded and published methods of recording ear drum complex movements include laser doppler vibrometry, laser digital holography, optical coherence tomography (OCT), laser triangulation. Infrared camera video recording of ear drum complex movement removes the need for a light or laser source. Ultrasound measurement of ear drum complex may also detect movement.

The tensor tympani muscle is controlled by the trigeminal nerve, which emerges from the brain, high in the brainstem. The branch to the tensor tympani muscle passes through a tunnel in the bones of the skull to the middle ear. It therefore is not affected by traumatic neck injuries and lower brainstem injuries (including strokes and intracranial bleeds). The ability to control middle ear muscles may also be preserved when a person has lost muscle power or control in other muscle groups, such as with motor neurone disease, or in those that may never have had good control from birth eg severe cerebral palsy.

In a further embodiment of the current invention, the ability to control communication, hearing aids and other multimedia and entertainment and other technologies in a silent technique is addressed. Current technologies can control these user interfaces with such methods as touch sensitive screens or displays, physical buttons, and voice sensitive commands and accelerometers. These methods are all either visible or audible, making control of these technologies obvious to people other than the user. This current invention allows the user to control these technologies along with any other connected user interface with an invisible and silent method.

The present invention is for a method of detecting voluntary ear structure movement, including drum complex movement, and using this to trigger a switch or other user interface.

SUMMARY OF THE INVENTION

The current invention is a method of detecting voluntary ear structure movement and using this to trigger a switch or other user interface which acts as a trigger for assistive technology, to allow a person who cannot currently communicate or control devices to have a further way to access and control these assistive technologies. The detection of ear drum movement has not previously been used to trigger assistive technologies.

The method for detecting voluntary movement of the ear drum complex (comprising the ear drum and malleus) in this invention is the use of a sensor wholly or partially sited in or adjacent to the ear canal, directed towards the ear drum complex. This sensor may be located in a structure worn like a hearing air, ear phone or earplug (subsequently jointly referred to as earphone). This sensor detects changes in the position or shape of the ear drum complex caused by voluntary movement of these structures by the user. Voluntary movements cause three dimensional change in shape and movement of the ear drum complex and also movement of the ear canal. The movement of the ear drum complex can be in a direction which is towards and away from the sensor located in the ear canal, or in a direction which is lateral to the sensor (which may be in perpendicular direction, such as movement of the malleus forward and backwards in relation to the face of the user).

Embodiments of the current invention include sensors which are imagers, including cameras, video cameras, or laser detectors, using any combination of visible or non visible spectrum light or infrared radiation, which are directed towards the ear drum complex. These sensors detect voluntary movement of the ear drum complex. Simple imagers will detect a two dimensional image of the ear drum complex. This image is communicated as an input to a processor that may be within the structure containing the sensor (earphone) or connected by wire or wirelessly in another device. Algorithm of the processor will analyse the two dimensional image and detects movement of the ear drum complex by changes in the image over time (image analysis). This image analysis will be individually configured according to the sensor involved to detect movement of an area of the ear drum complex, for example this may be a movement of a defined fixed point such as the lower end of the malleus, but may be any defined structure or reflection (the light reflex) on the ear drum complex. The imager may have an associated light source, such as LED emitting visible or infra red light, adjacent to the sensor and located within the sensor structure or earphone. The use of infra-red imagers may avoid the need for a light source as the ear structures emit infra-red thermal energy that can be detected as images due to body temperature.

In a further embodiment, sensors consisting of combined laser emitters and receivers, or combined ultrasound emitters and receivers detect movement of the ear drum complex towards and away from the sensor located in the ear canal. These embodiments include measurement methods using laser triangulation, optical coherence tomography, laser Doppler vibrometry and ultrasound to detect movement of the ear drum complex. The output from the sensors is communicated as an input to a processor that may be within the structure containing the sensor (earphone) or connected by wire or wirelessly in another device. Embodiments include the algorithm of the processor detecting a change in distance between the sensor and the eardrum complex, or by three dimensional analysis of the output detecting a change in the three dimensional shape of the ear drum complex.

The processor generates an output dependent on the algorithm detecting a movement of the ear drum complex of defined combination of duration and degree of movement that is defined to represent a voluntary contraction. The algorithm is configurable and programmed on an individual basis according to the specific sensor, application and user, to determine when the combination of degree and duration of movement detected is representative of a voluntary contraction. This output from the processor representing a voluntary contraction will be termed a "click". The output caused by the click is communicated to an attached device to trigger a change in the state of the attached device.

Attached devices include assistive technology that scans a graphical keyboard and the output of the processor of a click, selects the letter or word that is highlighted at the time of the generation of the click. This process copies the selected letter or word to a graphical window to allow communication by the user by text, or conversion to speech by an associated speech generator within the assistive technology device. The click may also select and highlight an icon on a graphical user interface and activate an associated function, in the same way that a mouse click can activate an application on a processor. Functions that may be activated may include, but are not limited to activating and controlling mobility aids, or home user interfaces such as switching on a room light.

A further advantage over existing assistive technology switches is that the location of the sensor wholly or partially in the ear canal anchors the sensor relative to the ear drum. With involuntary or voluntary head or neck movements the relative position of the sensor to the ear drum does not change, and so the sensor reliably detects voluntary movement irrespective of background head or neck movements. This allows accurate sensing of the triggering voluntary ear drum complex movements in patients unable to control head movements, and also when other movements can complicate the detection of trigger movements, such as in vehicles and during other motion. No complex external mounting devices are required to mount the sensor so that it is static in relation to the user. Also the sensor can trigger in people with involuntary movements such as athetoid cerebral palsy without being interfered with by the involuntary movements.

In another embodiment the sensor detects voluntary movements of the ear canal, which may be detected as a visible movement, or a change of the three dimensional shape of the ear canal, including by pressure on a microswitch or cross sectional area of the canal causing pressure changes on the ear sensor.

A further embodiment of this invention is the incorporation of the ear drum complex switch in hearing aids, to control hearing aid function such as including increasing or decreasing volume, switching on and off Bluetooth® communication.

Another embodiment of this invention is to provide silent and invisible control for user interfaces for any user. The ear drum complex switch method of this invention is able to control mobile phones, communication devices, home management devices and entertainment devices, and any other user output device or processor applications, that can be triggered by a user interface, through Bluetooth® communications or other links from the switch or its processor, to these devices. The ear drum complex switch can be used and worn like a hearing aid or earphone, or ear plug structure (subsequently jointly referred to as earphone), in or adjacent to the ear canal, and can be incorporated into other existing technologies such as hearing aids, earphones, and multi function ear devices which may include many functions including, telephone and entertainment audio play back, microphone for telephone, voice communication and voice commands, accelerometers, pulse oximetry, temperature sensors and any other sensors that are included (often termed smart "hearable" devices). This provides a means of silent and invisible control of user interfaces.

The processor associated with the sensor or within the connected user interface devices may be configured to respond to a multitude of combinations of different numbers and duration of voluntary ear movements or clicks. This is separately configurable according to the user interface device associated with the output from the processor. Examples would include a user interface with a mobile telephone which on receipt of an incoming telephone call will respond to one short click to answer the phone call, and two short clicks to send the call to answerphone service, or in a hearing aid associated sensor; one click may increase the volume and two short clicks to decrease the volume setting of the hearing aid.

Dynamic menu options will allow combinations of ear drum complex movements to select from multiple embedded menus which will be individually programmable for each user interface. For example, a menu may have a voice interface that activates the earphone speaker on receipt of a phone call to a Bluetooth® connected phone, and give the user several options by verbal description of the menu options. For example this could include one ear drum complex movement (subsequently termed a "click") to answer the call, two "clicks" in quick succession to send the call to answerphone message, and three "clicks" in quick succession to open a second voice menu to allow the user to send a selection of predefined text messages. This allows users to manage incoming phone calls silently and invisibly such as in a meeting, or social event. Using input from an ear drum movement switch device in each ear allows more complex controls in users who learn to control each ear drum complex movement independently. Two sensors (one in each ear) are able to generate inputs similar to a left and right mouse click respectively.

An embodiment incorporating a microphone in the earphone containing the sensor, allows the processor to process the input from the sensor in conjunction with input from the microphone. The algorithm of the processor can be used to exclude involuntary movement of the ear structures (which can occur due to loud noises) from incorrectly triggering an output signal or click, by excluding eardrum complex movements from generating an output when these are simultaneous with a loud noise detected by the microphone.

BRIEF DESCRIPTION OF THE DRAWING FIGURES

DETAILED DESCRIPTION OF THE INVENTION

The present invention describes a sensor worn by a user in or adjacent to the ear canal, with sensor directed towards the ear drum complex, which generates an input to a user interface to trigger an action by the processor within the user interface.

Figure 1:
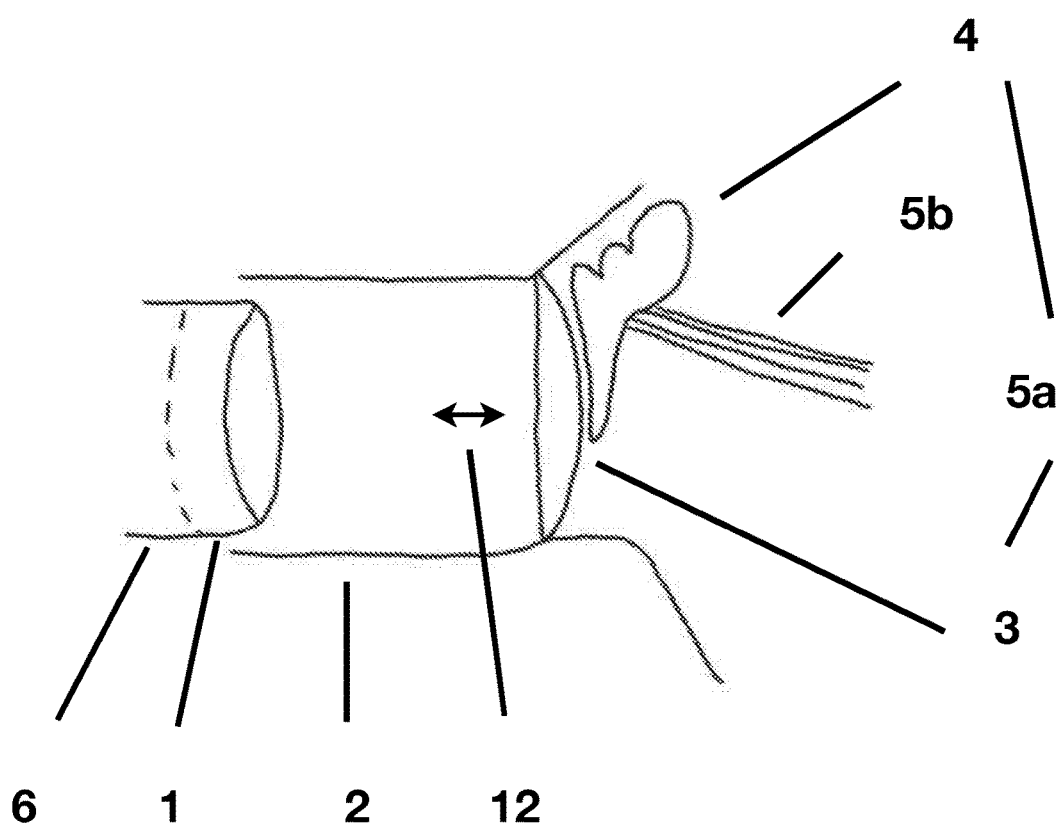
FIG. 1 shows a pictorial representation of a cross section of the right ear canal and partial view of middle ear showing the sensor in the ear canal in relation to ear drum, malleus and tensor tympani muscle.

FIG. 1 illustrates one embodiment of the sensor 1, as a cross sectional view of the right ear canal 2. The sensor being located in the ear canal 2, with the sensor being part of an ear phone, hearing aid or ear plug assembly 6. The sensor is directed towards the ear drum complex 5a, partially consisting of the ear drum (tympanic membrane) 3 and the malleus 4 (a middle ear bone) that is connected to the inner aspect of the ear drum 3. Movement of the ear drum complex 5a, which may be towards or away 12 from the sensor, or in a lateral direction 13 (FIG. 2), (which may be in a direction that is similar to a perpendicular direction, such as a movement of the malleus forwards and backwards relative to the users face), is detected by the sensor. The sensor 1 may have a configuration including an imager, which may be a video camera or an infrared video camera, with or without light source, or have a laser emitting and receiving combination which may have a static or scanning laser element (including laser Doppler vibrometry, Optical coherence tomography, laser triangulation), or an ultrasound or other high frequency sound emitter and receiver, or a combination of these. The tensor tympani 5b is a muscle that is attached to the malleus 4. When the tensor tympani 5b contracts the malleus 4 is moved and this causes movement of the attached ear drum 12 and 13 (in FIG. 2). This movement 12, 13 (in FIG. 2) is detected by the sensor 1.

Figure 2:
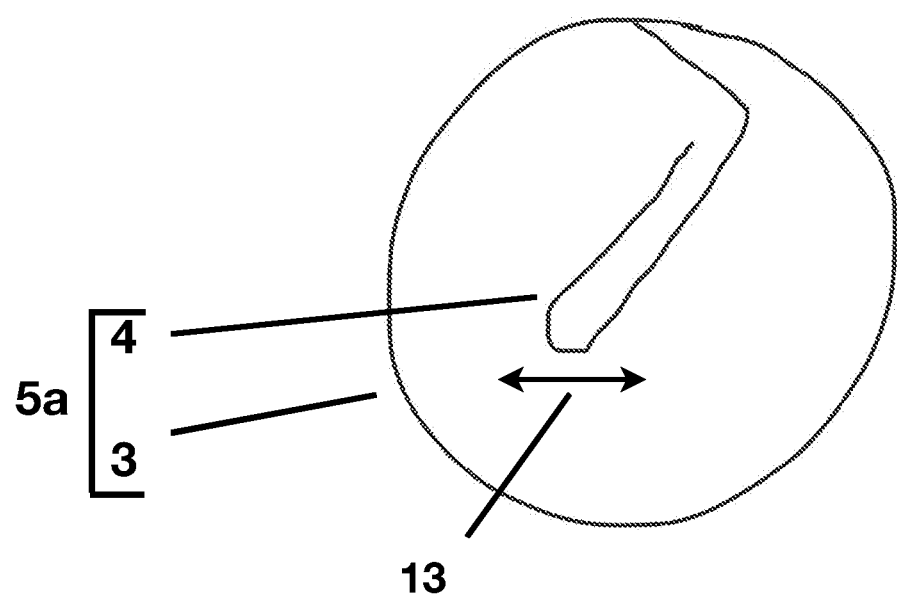
FIG. 2 is a schematic view of the external aspect of a right ear drum showing the impression of the embedded malleus bone.

FIG. 2 illustrates the external view of the ear drum complex 5a, showing the ear drum 3 and the malleus 4 which is visible through the ear drum 3, where it is located attached to the inner aspect of the ear drum 3. The lateral movement 13 of the ear drum which can be voluntarily controlled is demonstrated and is detected by the sensor which is directed to the external surface of the ear drum complex 5a.

Figure 3:
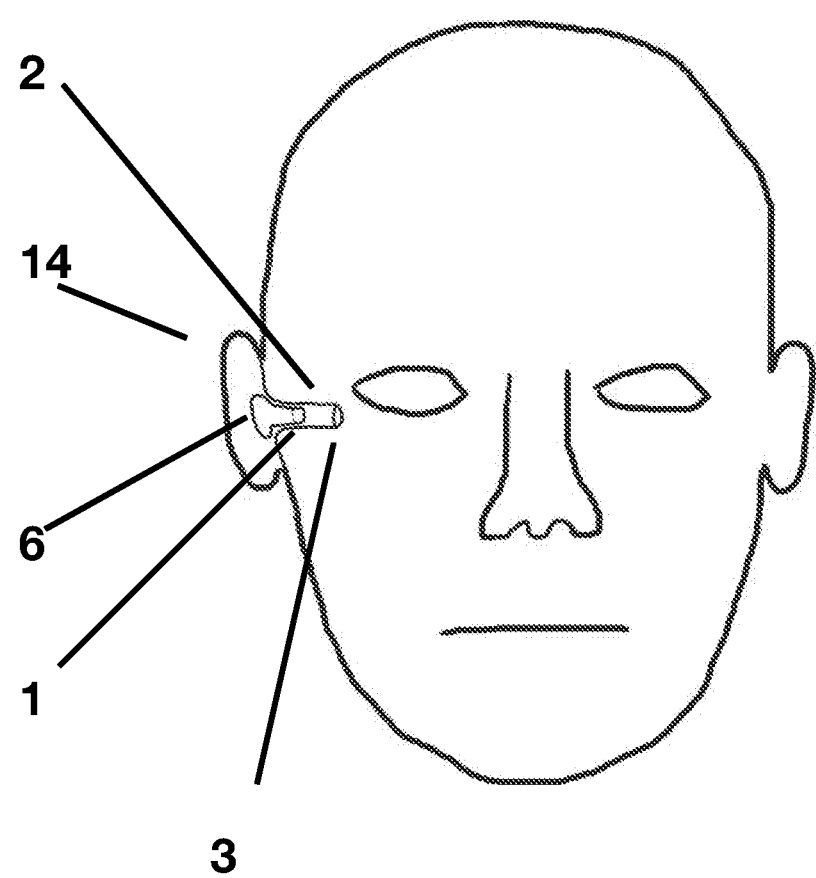
FIG. 3 is a pictorial representation of the sensor worn as an earphone in the right ear canal.

FIG. 3 demonstrates the sensor 1 as one embodiment configured in an earphone or ear plug or hearing aid structure 6 (subsequently jointly referred as earphone) with the sensor 1 being positioned (worn) partially within the ear canal 2, with the external aspect being located within the external ear (pinna) 14. The sensor 1 is directed towards the ear drum 3. Other embodiments include the sensor 1 being located in a structure totally within the ear canal 2 or situated (worn) within or adjacent to the external ear 14, either as an individual structure or physically connected to a similar structure adjacent to the other external ear 14.

Figure 4:
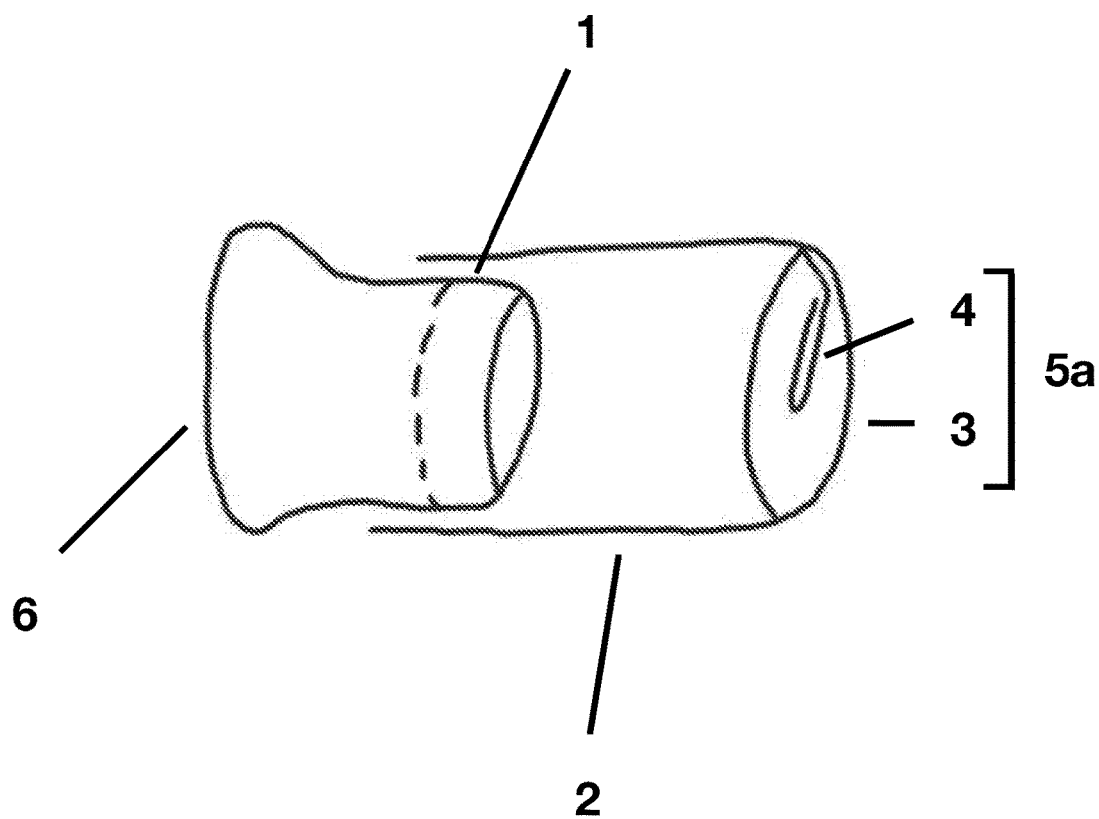
FIG. 4 is a pictorial representation of the ear sensor located partially within the ear canal close to the ear drum.

FIG. 4 demonstrates the sensor 1, within the earphone 6, partially sited within the ear canal 2, directed towards the ear drum complex 5a, showing the ear drum 3, and the malleus 4. In a further embodiment, the sensor 1 is triggered by voluntary movement of the ear canal 2. Methods of detecting this movement include by detecting a visible movement of the ear canal 2 by a camera sensor 1, or by pressure sensor 1 within the earphone, hearing aid or ear plug assembly 6. This sensor may be a simple microswitch detecting movement of the ear canal wall 2 against the switch, or in another configuration the sensor is a pressure sensor 1 occupying the canal and is deformed by the change in three dimensional shape of the canal causing a pressure change that is detected by the sensor 1.

Figure 5:
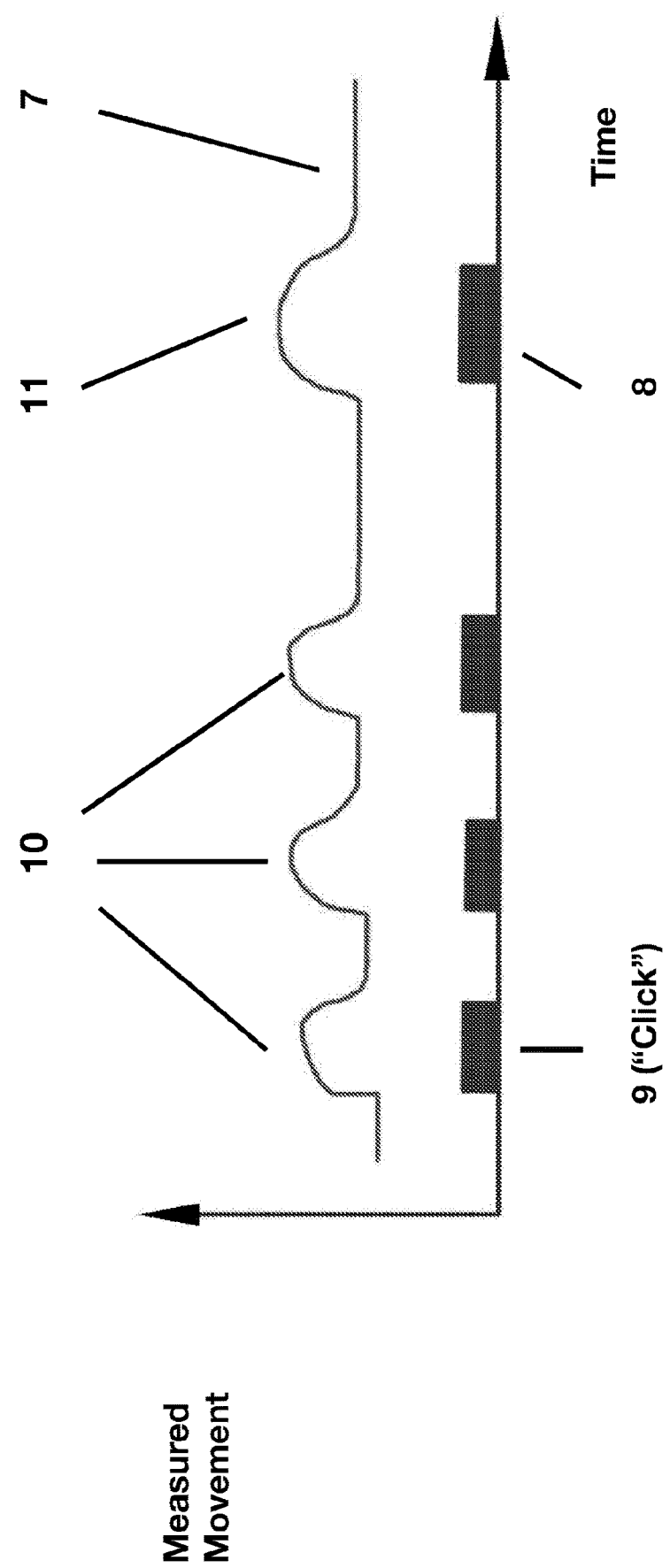
FIG. 5 is a graphical representation of the recorded movement of the malleus with voluntary ear drum complex movement, recorded and analysed using a video recording sensor.

FIG. 5 shows a graphical representation of the measurement of movement of the malleus 4 detected by sensor 1 being one embodiment where the sensor 1 is a video camera with associated LED light source within the earphone structure 6. In this embodiment the camera within the sensor 1 may use any fixed point on the ear drum complex 5a to record movement 12, 13 and, for example, it may record position of the lower end of the malleus 4. This position is recorded by a video camera sensor 1 and the position is represented as a line on the graph 7, where they axis represents position and measurement of movement, and the x axis represents time. Voluntary movements 11, 12, 13 of the ear drum complex 5a are represented on the diagram as shaded blocks 8. These voluntary movements 11,12,13,8 cause movement of the malleus 4 and the change of position (movement 12,13) of the malleus 4 and the ear drum 3 (ear drum complex 5a). This change of position of the malleus 4 detected by the sensor 1 is shown as a deflection of the line 7. A voluntary movement 8, 12, 13 of the ear drum complex 5a is shown 10 as a change in line 7, and will be subsequently referred to as a "click" 9. A series of short "clicks" 10 is shown, and a more prolonged ear drum complex movement or prolonged "click" 11 is also shown.

Figure 6:
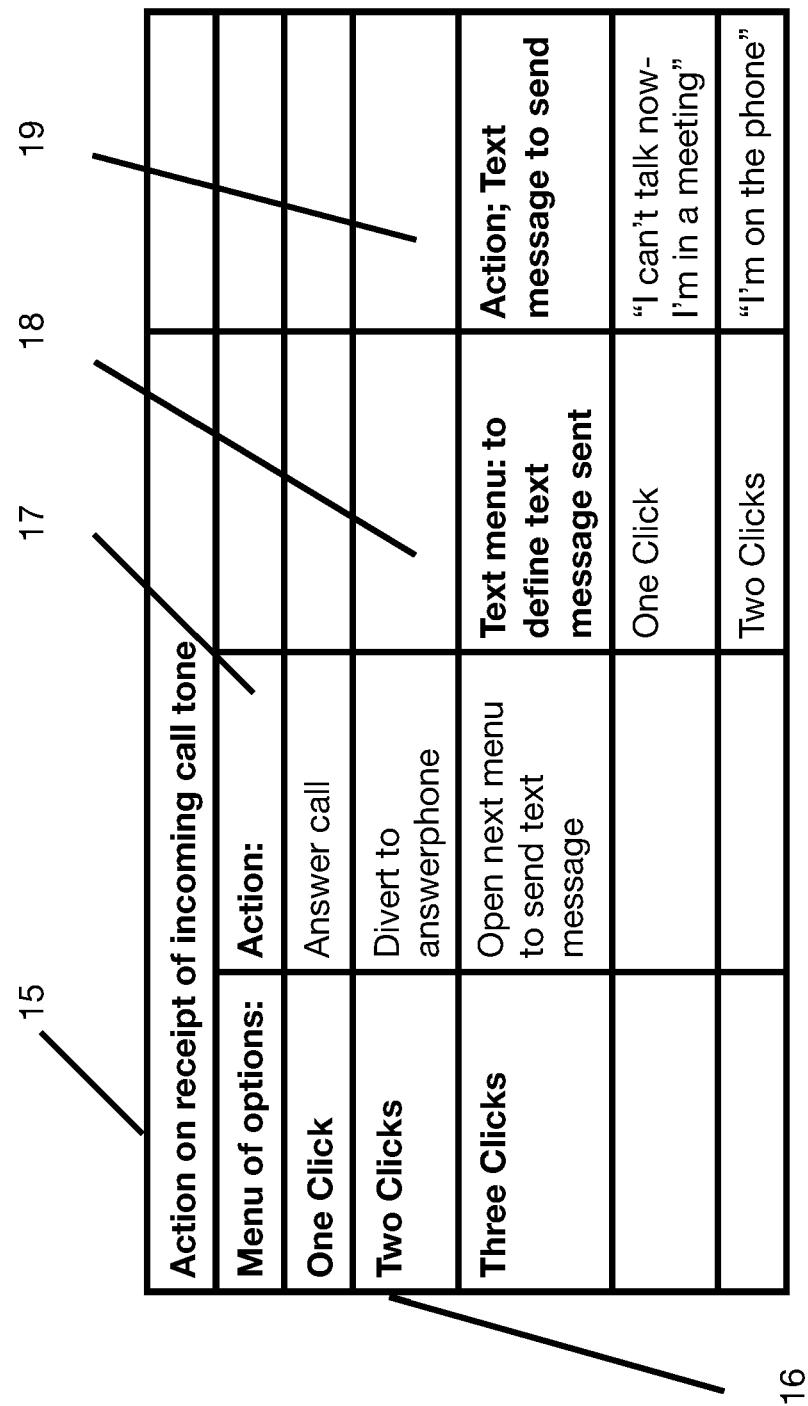
FIG. 6 is a table showing an example of an audible menu that would be controllable by voluntary ear drum complex movement.

FIG. 6 show an example of an embodiment of the current invention as a user interface to control a telephone with the sensor incorporated into an earphone linked by any means to a telephone.

The menu 15 demonstrates an audible menu that would be able to be presented to the user by means of computer generated voice prompts through the earphone when an incoming telephone call is detected. The menu of options is read out to the user, and the user then performs one or a series of voluntary ear drum complex 5a movement "clicks" 9, 16 to determine the telephone's action 17. Examples include that the call is answered, the call is diverted to answer machine, or that a predefined text message is sent back to the caller. The latter may be selectable from a second sub menu 18, with output of text message being further determined by a menu of combination of clicks read to the user through the earphone. This may include a response such as "can't talk now. I'm in a meeting" 19. These are examples as the menus, messages and configuration of clicks would be configurable.

Figure 7:
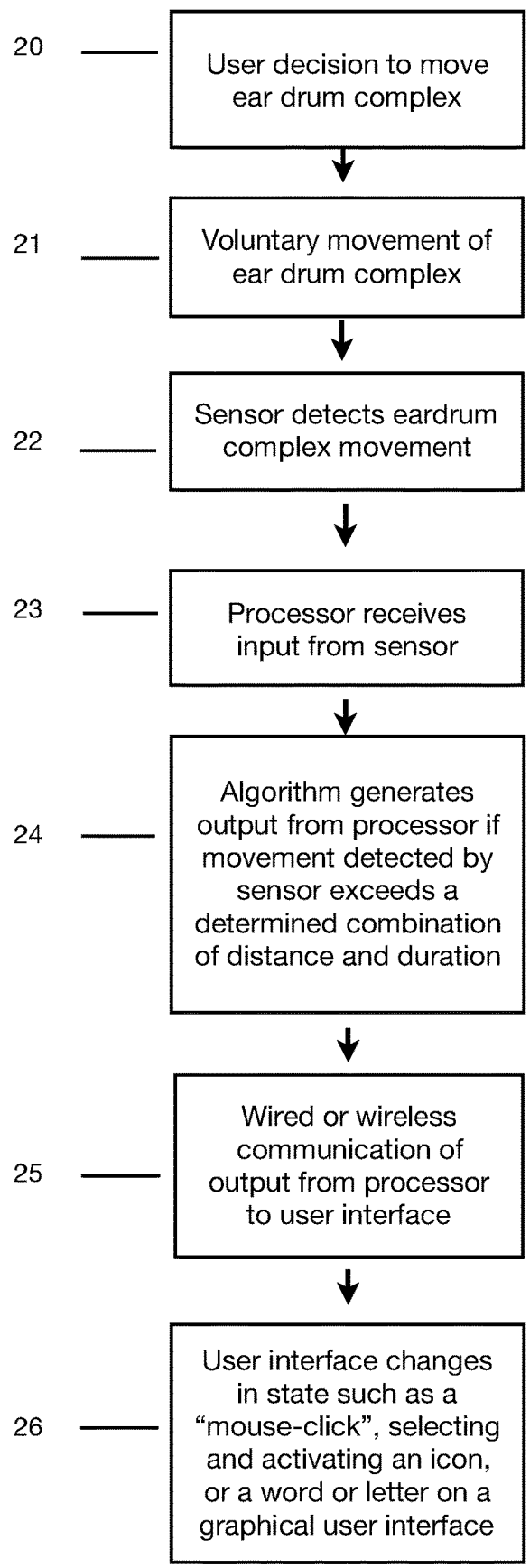
FIG. 7 is a flow chart of an embodiment showing triggering of assistive technologies.

FIG. 7 is a flow chart of an embodiment showing triggering of assistive technologies. The user decides to generate a trigger 20, such as to highlight and select a letter on a scanning keyboard on a graphical user interface, as a communication tool to generate a text sentence on a computer screen. The ear drum complex is moved 12,13,8,9,10 by the voluntary contraction of muscle in the middle ear 21. The sensor 1 detects the voluntary movement of the ear drum complex 22. The processor 23, (which in an embodiment may be located in the earphone 6 structure, or in a wired or wirelessly connected processor remote from the earphone structure 6), receives input from the sensor 1. An algorithm 24 of the processor, which will be configurable to user and dependent on specific use, will generate an control output (also known as a trigger) when the combination of amount and duration of the movement 8, 10, 11, 12, 13 detected by the sensor 1 represents a voluntary movement of the ear drum complex 5a or also known as a "click" 9. The output from the processor is communicated to a user interface by wired or wireless communication 25. The assistive technology user interface changes the state of the graphical user interface by graphically highlighting and selecting the letter that the scanning cursor is currently highlighting at the time of receiving the click. The selected letter is added to a graphical text display and progressive selection of letters will generate user communication by text 26. This embodiment includes the ability to generate speech, type text, and activating a multitude of other assistive user interfaces.

Figure 8:
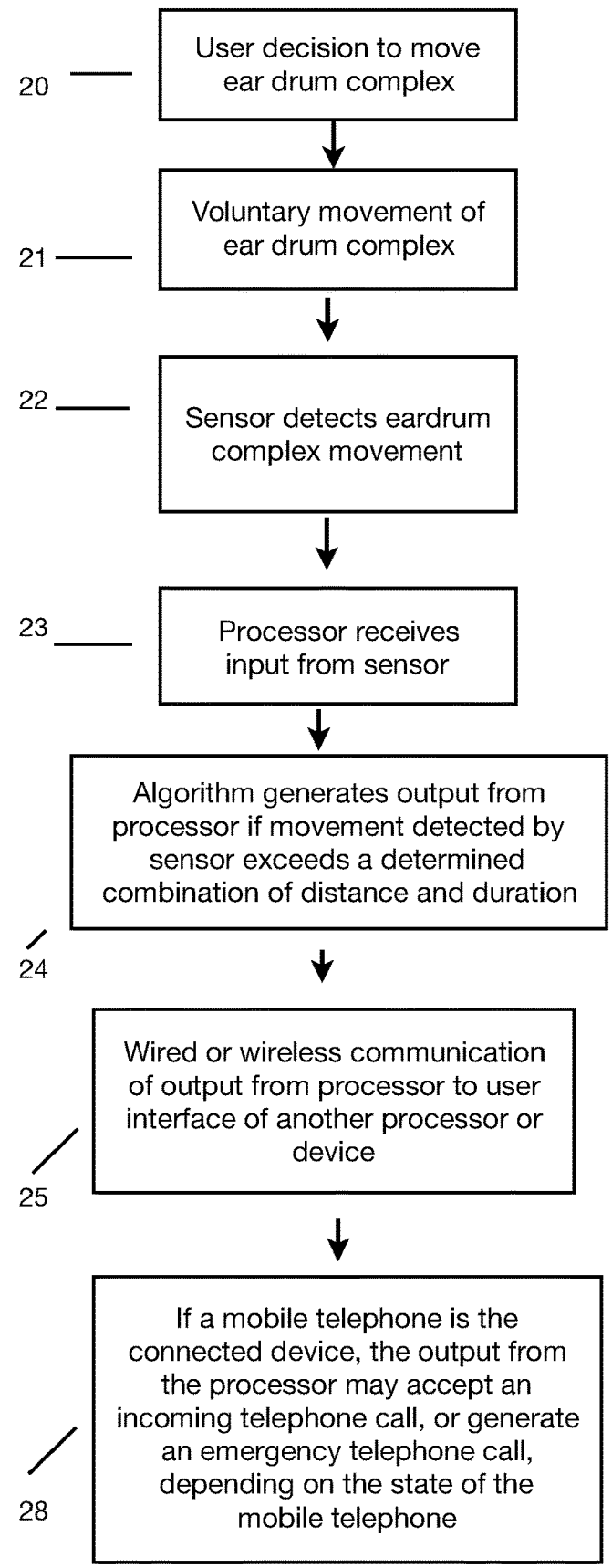
FIG. 8 is a flow chart of an embodiment showing triggering of other user interfaces and technologies.

FIG. 8 is a flow chart of an embodiment showing triggering of other user interfaces and technologies which may include, but is not limited to telephones, communication devices, and entertainment devices, and any other device by triggering processor applications. The user decides to generate a trigger 20, such as to highlight and activate a menu selection which may be a graphical menu on the user interface device, or presented as a spoken menu, or may be a predefined trigger on a simple device such as volume up or down commands for a hearing aid, or controlling a telephone to accept an incoming telephone call. The ear drum complex is moved 12,13,8,9,10 by the voluntary contraction of muscle in the middle ear 21. The sensor 1 detects the voluntary movement of the ear drum complex 22. The processor 23, which in an embodiment may be in the earphone 6 structure, or in a wired or wirelessly connected processor remote from the earphone structure 6, receives input from the sensor 1. An algorithm 24 of the processor, which will be configurable to user and dependent on specific use, will generate an control output (also known as a trigger) when the combination of amount and duration of the movement 8, 10,11,12, 13 detected by the sensor 1 represents a voluntary movement of the ear drum complex 5a or also known as a "click" 9. The output from the processor is communicated to a user interface, or processor of another device by wired or wireless communication 25. An example of the resultant action on this device, such as a mobile telephone, is to accept an incoming telephone call or to activate an application on a mobile telephone to generate an emergency telephone call 28.

What is claimed is:

1. A method of triggering electronic switch and user interfaces by a sensor located in the ear canal or near to the ear canal, said method comprising:
   detecting effects of:
   (i) voluntary contraction of a tensor tympani muscle, by detecting resultant movements of, or changes in position or shape of, a tympanic membrane or a malleus using the sensor; and
   (ii) involuntary movements of, or changes in position or shape of, the tympanic membrane or the malleus using the sensor;
   communicating the effects resulting from voluntary contractions and involuntary movements, changes in position or shape to a processor;
   excluding, by the processor, the effects resulting from involuntary movements, changes in position or shape; and
   generating an output by the processor, based upon the effects resulting solely from the voluntary contractions, to affect the function of a connected device.

2. The method of claim 1, wherein detection of voluntary contraction of a middle ear muscle is detected by the sensor which detects movement of the tympanic membrane or the malleus.

3. The method of claim 1, wherein the sensor is located wholly or partially within the ear canal.

4. The method of claim 1, wherein the sensor detects movement of the tympanic membrane, or the malleus bone, relative to a position of the sensor.

5. The method of claim 1, wherein movement of the tympanic membrane or malleus is detected by:
(i) two dimensional analysis of an image of a surface of the tympanic membrane and malleus;
(ii) measuring changes in distance from the tympanic membrane or malleus to the sensor; or
(iii) detecting change in a three dimensional shape of a combined tympanic membrane and malleus structure.

6. The method of claim 5, wherein the sensor is an imager including a camera located in the ear canal.

7. The method of claim 6, wherein the tympanic membrane is illuminated by a light source to enable the imager to record movement of the tympanic membrane and malleus.

8. The method of claim 6, wherein the imager is an infra-red camera which detects images of the tympanic membrane and malleus.

9. The method of claim 5, wherein movement of the tympanic membrane or malleus towards or away from the sensor is detected by:
(i) laser Doppler vibrometry, digital laser holography, optical coherence tomography, laser triangulation or other laser measurement analysis; or
(ii) any measurement process which measures the change in distance from the sensor to an ear drum complex, including using ultrasound, visible or non-visible spectrum light analysis, or other proximity sensor.

10. The method of claim 5, wherein the three dimensional shape of the combined tympanic membrane and malleus structure is detected by:
(i) optical coherence tomography, digital laser holography or other laser measurement analysis; or
(ii) any measurement process that records the three dimensional shape, including using ultrasound, visible, and non visible spectrum light analysis.

11. The method of claim 1, wherein the sensor is located adjacent the ear canal at a location that is either in or close to the external ear.

12. The method of claim 1, wherein the sensor is incorporated into a hearing aid, which is configured to be located in the ear canal, or adjacent the ear canal at a location that is either in or close to the external ear.

13. The method of claim 1, wherein the method is incorporated:
(i) in an earphone incorporating any combination of hearing improvement function, microphone, audio playback including telephone receiver, health monitoring, temperature and oxygen saturation monitoring, head movement by accelerometer, and voice communication using a microphone, camera or any other in-ear located device; or
(ii) into any device worn in or adjacent to the ear canal.

14. The method of claim 1, wherein the processor is configured to determine that:
(i) a degree and duration of movement, or change in shape or position of the tympanic membrane or malleus, is sufficient to represent a voluntary contraction of the tensor tympani muscle; and/or
(ii) the degree of movement, or change in shape or position of the tympanic membranes or malleus, is any combination of greater magnitude, faster or more prolonged than background involuntary movement of the tympanic membrane or malleus.

15. The method of claim 1, wherein the processor is housed in a structure partially or wholly located in the ear canal, wherein the structure also contains the sensor.

16. The method of claim 1, wherein the processor is connected to the sensor by wire or by wireless communication.

17. The method of claim 1, wherein the output generated by the processor:
(i) triggers a change in a status of a hearing aid containing the sensor;
(ii) triggers a change in a connected user interface; or
(iii) triggers a change in any connected device, technology or computer application or program within a connected technology, device or processor.

18. The method of claim 17, wherein the output signal from the processor triggers:
(i) a user interface change, to include highlighting and selecting items on a graphical user interface, change a state of an electronic device, or to perform any command on a receiving processor;
(ii) a command on a communication device, mobility device, home management device or any other user output device which can be triggered through a user interface.

19. The method of claim 17, wherein a user interface device is triggered by a multitude of movements or change in shape or position of the tympanic membrane or malleus, with different options activated dependent on a number or duration of the movements or changes of shape or position.

20. The method of claim 17, wherein a speaker within an earphone containing the sensor presents an audible menu of options to a user as speech or other audible notifications from the processor or linked user interface, and the audible menu is configured to trigger interfaces defined by different combinations of multiple voluntary movements or changes of shape or position of the tympanic membrane or malleus of the user.

21. The method of claim 20, wherein the menu selections are determined by the processor according to changes in state of the processor or linked user interface, or an incoming phone call to a linked mobile phone.

22. An apparatus for triggering electronic switch and user interfaces, said apparatus comprising:
a processor; and
a sensor that is locatable in, or near to, an ear canal,
wherein the sensor is configured to detect effects of:
(i) voluntary contraction of a tensor tympani muscle, by detecting resultant movements of, or changes in position or shape of, a tympanic membrane or a malleus; and
(ii) involuntary movements of, or changes in position or shape of, the tympanic membrane or the malleus;
wherein the sensor is configured to communicate the effects resulting from voluntary contraction and involuntary movements, changes in position or shape as an input to the processor;
wherein the processor is configured to exclude the effects resulting from involuntary movements, changes in position or shape; and
wherein the processor is configured to generate an output, based upon the effects resulting solely from the voluntary contractions, to affect a function of a connected device.

23. The apparatus as claimed in claim 22, wherein the apparatus is a hearing aid, arranged to be locatable in the ear canal, or adjacent to the ear canal at a location that is either in or close to the external ear.

24. The apparatus as claimed in claim 22, wherein the apparatus is an earphone incorporating any combination of the group comprising: hearing improvement function; microphone; audio playback, including telephone receiver; health monitoring; temperature and oxygen saturation monitoring; head movement, by accelerometer; voice communication, using a microphone; camera; and/or any other in-ear locatable device.

* * * * *